(12) United States Patent
Levine

(10) Patent No.: US 7,828,760 B2
(45) Date of Patent: Nov. 9, 2010

(54) WEIGHT DRIVEN NECK TRACTION UNIT AND METHOD

(75) Inventor: Jason M. Levine, 7571 SW. 150th St., Miami, FL (US) 33158

(73) Assignees: Jason M. Levine, Coral Gables, FL (US); Mike Gorman, Coral Gables, FL (US)

( * ) Notice: Subject to any disclaimer, the term of this patent is extended or adjusted under 35 U.S.C. 154(b) by 249 days.

(21) Appl. No.: 12/111,587

(22) Filed: Apr. 29, 2008

(65) Prior Publication Data

US 2009/0270783 A1  Oct. 29, 2009

(51) Int. Cl.
*A61F 5/00* (2006.01)
(52) U.S. Cl. .................................................. 602/32
(58) Field of Classification Search ............ 602/18, 602/5, 1, 32–35, 38–40
See application file for complete search history.

(56) References Cited

U.S. PATENT DOCUMENTS

| 3,648,308 | A |   | 3/1972  | Greenawalt  | 5/338   |
|-----------|---|---|---------|-------------|---------|
| 3,768,464 | A | * | 10/1973 | Greissing   | 602/32  |
| D229,359  | S |   | 11/1973 | Nightingale | D83/1 E |
| 4,166,459 | A |   | 9/1979  | Nightingale | 128/75  |
| D272,467  | S |   | 1/1984  | Nightingale | D24/64  |
| 4,593,684 | A |   | 6/1986  | Graham      | 128/75  |
| 4,784,122 | A |   | 11/1988 | Graham      | 128/75  |
| 4,832,007 | A |   | 5/1989  | Davis, Jr. et al. | 128/70 |
| 5,067,483 | A | * | 11/1991 | Freed       | 602/18  |
| D330,083  | S |   | 10/1992 | Nightingale | D24/188 |
| 5,451,202 | A | * | 9/1995  | Miller et al. | 602/36 |
| D431,080  | S |   | 9/2000  | Anderson    | D24/188 |
| 6,217,538 | B1 |  | 4/2001  | Anderson    | 602/35  |
| 6,875,189 | B1 |  | 4/2005  | Nelson      | 602/17  |
| 2001/0029345 | A1 | | 10/2001 | Anderson | 602/35 |
| 2007/0055306 | A1 | * | 3/2007 | Han | 606/237 |
| 2007/0118991 | A1 | | 5/2007 | Nakayama | 5/640 |

FOREIGN PATENT DOCUMENTS

JP    3374272    11/1997

* cited by examiner

*Primary Examiner*—Patricia M Bianco
*Assistant Examiner*—Tarla R Patel
(74) *Attorney, Agent, or Firm*—Robert C. Kain, Jr.

(57) ABSTRACT

The neck traction device elongated a user's neck with the application of force on the user's shoulders. One embodiment includes a head pad, a vertically movably head support frame, a pivotally connected linkage member coupled to a shoulder frame element. The shoulder frame and shoulder pads are longitudinally movably mounted and the linked system exerts a longitudinal force on the user's shoulders when the user's head rests on the head pad and depresses the head pad. A biasing mechanism either upwardly supports the head frame or longitudinally limits the extension of the shoulder frame such that when the head is lifted off the head frame, the biasing mechanism raises the head pad and moves back the shoulder frame and pads. Alternatively, a transmission may be used to convert the substantially downward force due to the head weight to a longitudinal force on the shoulder pads.

10 Claims, 3 Drawing Sheets

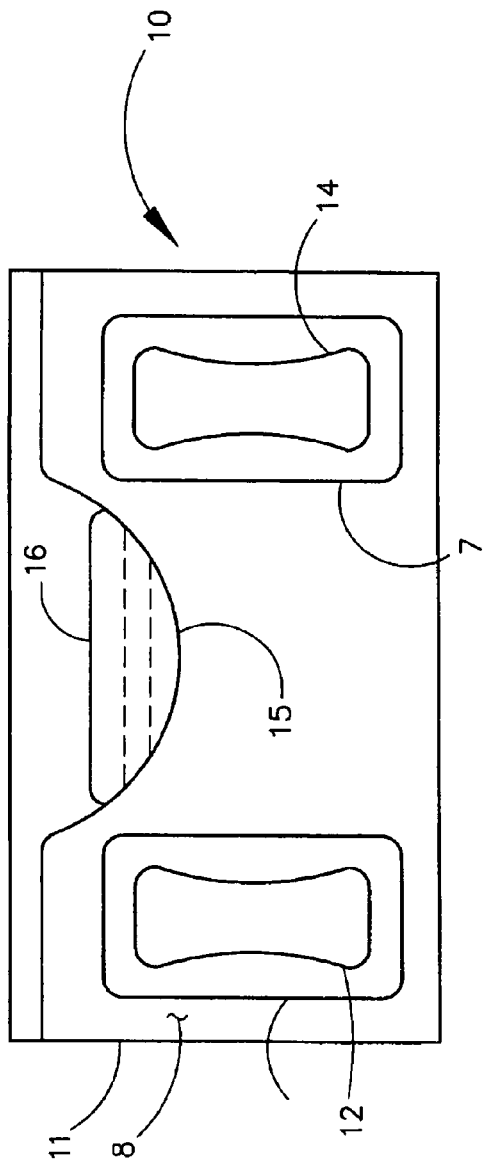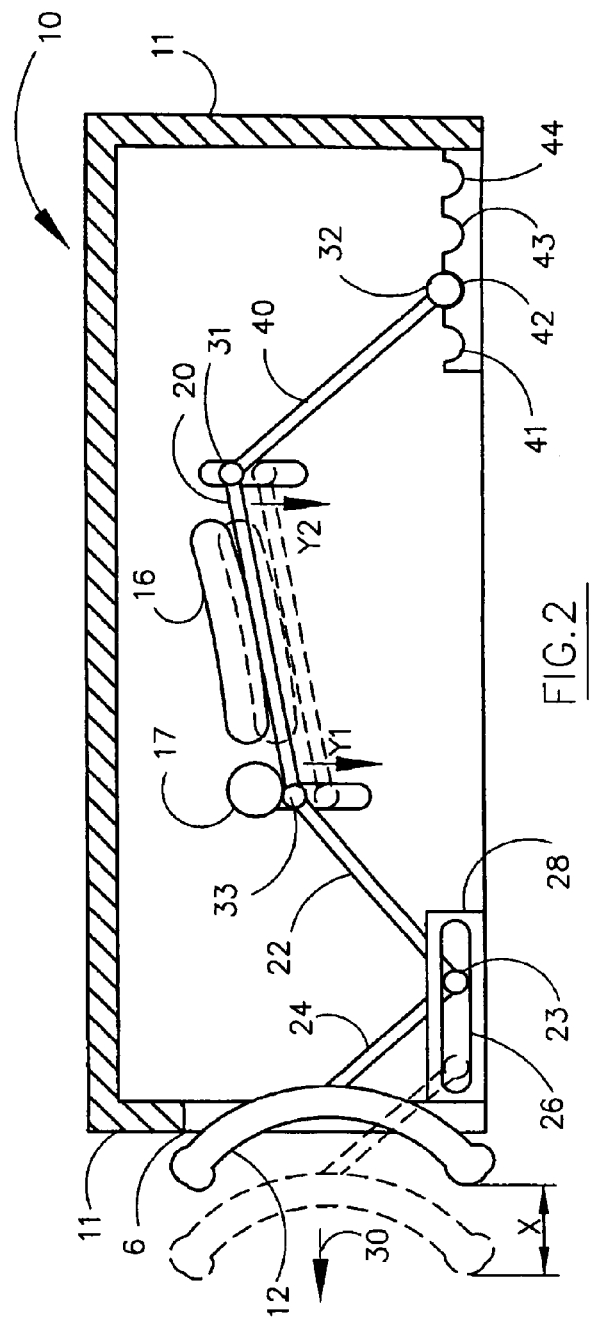
FIG.1
FIG.2

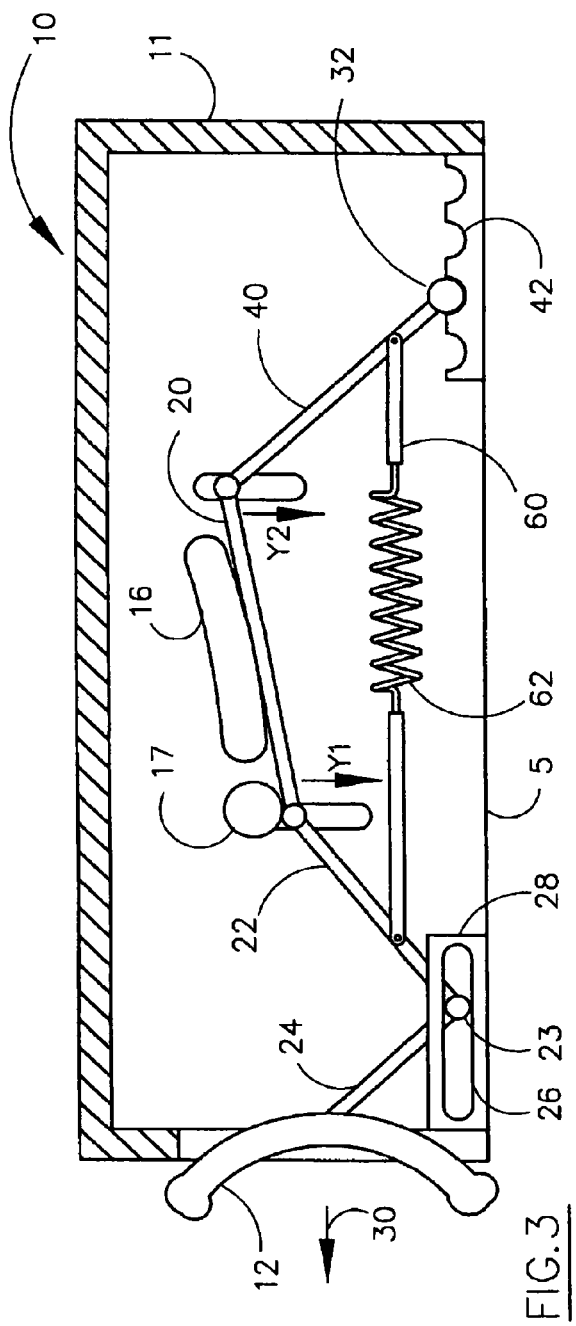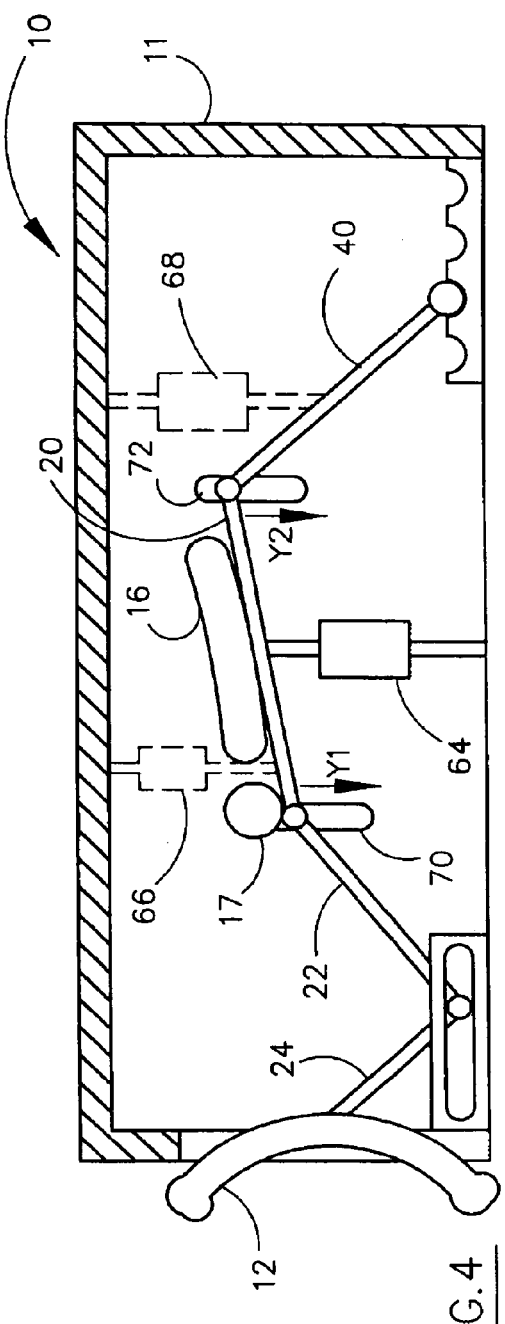

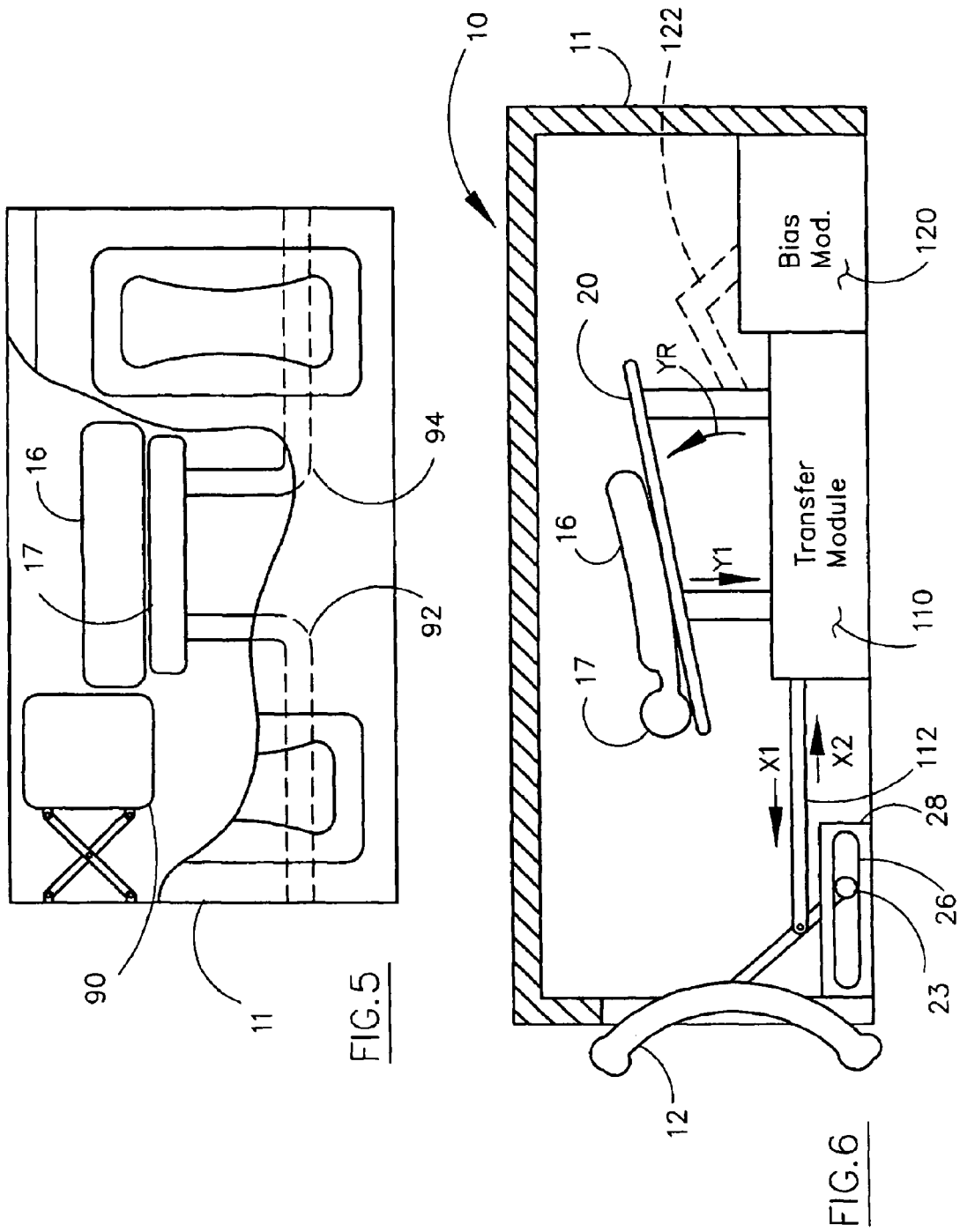

WEIGHT DRIVEN NECK TRACTION UNIT AND METHOD

The present invention relates to a weight driven neck traction unit and a method.

BACKGROUND OF THE INVENTION

Various neck traction systems are found in the prior art. U.S. Patent Publication U.S. 2007/0055306 A1 to Han discloses a traction apparatus for the cervical vertebrae and shows a neck traction unit wherein the user has manual longitudinal adjustment and manual elevational adjustment. Han '306 utilizes manual screw drive controls to elevate the head and manual screw drive control to elongate and provide neck traction. These manual screw controls may be replaced by motor driven screw drives.

U.S. Patent Publication US 2007/0118991 A1 to Nakayama discloses a pillow with internal elevational springs. Nakayama '991 does not disclose a traction system which transfers downward head weight to a longitudinal extension for neck traction.

U.S. Pat. No. 5,067,483 A to Freed discloses a cervical traction device and shows an angled traction unit with a powered, down-angle extension element for the shoulder pads. Freed '483 does not utilize the weight of the head of the user to develop neck traction.

Other traction systems are shown in: U.S. Patent Publication US 2001/0029345 A1 to Anderson for Cervical/Upper Thoracic Relaxer (traction stand); U.S. Pat. No. 6,875,189 B1 to Nelson for Cervical Traction Device; U.S. Pat. No. 6,217,538 B1 to Anderson for Cervical/Upper Thoracic Relaxer (traction stand); U.S. Pat. No. 4,832,007 A to Davis for Traction Pillow and Method shows a pillow with air release channels; U.S. Pat. No. 4,784,122 A to Graham for Portable Cervical Traction Device using Constant Force Springs; U.S. Pat. No. 4,593,684 A to Graham for Occipital Support for Cervical Traction; U.S. Pat. No. 4,166,459 A to Nightingale for Cervical Traction Unit; U.S. Pat. No. 3,648,308 A to Greenawalt for Elevated Traction Pillow; U.S. Design Pat. No. D 431,080 S to Anderson for Combined Cervical and Upper Thoracic Relaxer shows a traction stand; U.S. Design Pat. No. D 330,083 S to Nightingale for Cervical Traction Unit; U.S. Design Pat. No. D 272,467 S to Nightingale for Cervical Traction Unit; U.S. Design Pat. No. D 229,359 S to Nightingale Cervical Traction Halter; and Japanese Patent Publication JP 3374272 B2 to Matsuoka.

OBJECTS OF THE INVENTION

It is an object of the present invention to provide a neck traction device and a neck traction method.

It is a further object of the present invention to provide a neck traction device and method which utilizes the weight of the user's head and a transmission or transfer system which transfers the weight to a longitudinal force applied on shoulder pads on each of the user's shoulder.

It is another object of the present invention to provide a biasing means to counteract the head weight such that the head pad rises when the user lifts his or her head from the head pad.

SUMMARY OF THE INVENTION

The neck traction device is adopted to longitudinally elongate a user's neck with the application of force on the user's left and right shoulder while supporting the user's head in a substantially longitudinally stationary position. The device includes, in one embodiment, a head pad for the user's head and a pair of shoulder's pad for the user's shoulder. The head pad is mounted on a head support frame which is substantially vertically movably mounted within a support structure. The shoulder pads are mounted on a shoulder frame element which is longitudinally movably mounted in the support structure. In one embodiment, a linkage member pivotally connects the head support frame and the shoulder frame such that a substantially downward force due to the user's head weight on the head pad is transferred via the head support frame to the shoulder frame element which then exerts a longitudinal force on the shoulder pads of the user. The shoulder pads and frame extend out and move longitudinally. A biasing mechanism either upwardly biases the head support frame or longitudinally limits the extension of the shoulder frame element, the latter having the effect that when the head of the user is lifted off the head frame element in head pad, the biasing mechanism raises the head pad. Of course, this also pulls back the shoulder pads from an extended position when the head is on the head pad, to a rest position inboard of the support structure and thereby withdrawing the neck traction on the user's neck. Alternatively, a transmission may be used to convert the substantially downward force due to the head weight of the user's head to a longitudinal force on the shoulder pads. Further, the biasing element may be disposed on the shoulder pad frame, on the head support frame or on intermediate linkages to achieve the same result, that is, the upward movement of the head pad when the user's head is withdrawn from the head pad and the longitudinal contraction of the shoulder pads from an extended position to a withdrawn or non-extended position inboard of the support structure.

BRIEF DESCRIPTION OF THE DRAWINGS

Further objects and advantages of the present invention can be found in the detailed description of the preferred embodiments when taken in conjunction with the accompanying drawings in which:

FIG. 1 diagrammatically illustrates a front elevational view of the weight driven neck traction unit;

FIG. 2 diagrammatically illustrates, in schematic form, an internal side view of certain components of the neck traction device in accordance with the principles of one embodiment of the present invention;

FIG. 3 diagrammatically illustrates an internal view of one embodiment of the neck traction device;

FIG. 4 diagrammatically illustrates a schematic internal view of another embodiment of the neck traction device;

FIG. 5 diagrammatically illustrates side pillows on either side of the head pad;

FIG. 6 diagrammatically illustrates an internal schematic of a further embodiment of the neck traction device.

DETAILED DESCRIPTION OF THE PREFERRED EMBODIMENTS

The present invention relates to a weight driven neck traction unit and method. Similar numerals designate similar items throughout the drawings.

FIG. 1 diagrammatically illustrates the front 8 of neck traction device 10. The front panel or wall 8 includes shoulder pad openings 6, 7 and shows shoulder pads 12, 14 thereat. Front wall 8 of supporting structure 11 has a neck cutout 15.

Head pad 16 is visible through cutout 16. The size and proportional dimensions of traction unit 10 may be different than shown in these drawings.

FIG. 2 diagrammatically illustrates internal working components of one embodiment of neck traction device 10. In this embodiment, head pad 16 is mounted on head frame element 20. Back of neck cushion 17 is also mounted on head pad frame 20. As shown in FIG. 4, the back of neck cushion 17 may be part of head pad 16.

Returning to FIG. 2, an inter-linking connecting element 22 has one end pivotally attached to head pad frame element 20 and the other end pivotally attached to shoulder frame element 24. Shoulder pad 12 is attached to shoulder pad frame element 24. Proximal end 23 of interconnecting linkage 22 longitudinally moves with respect to support structure 11 due to movement in channel track 26 of track mount 28. Additional track mounts (mounted at lateral positions behind front wall 8) may be utilized to assure that shoulder pads 12, 14 move in a consistent longitudinal manner as shown in direction x and arrow 30. In operation, when the user places his or her head on head pad 16, a downward force is created by the weight of the user's head and head pad support element 20 moves substantially vertically downward as noted by directions y1 and y2. This downward motion is shown by the dashed lines in FIG. 2. The downward motion is transferred via interconnecting linkage 22 to shoulder pad frame support 24. The linkage and track mount 26, 28 converts or transforms vertical movement into longitudinal movement. Shoulder pad 12 then moves direction x and thereby provides elongated traction between the head of the user substantially statically supported on head pad 16 and the shoulders of the user. Items closer to shoulder pad 12 are "proximate" other items which are farther away or "distally" disposed with respect to shoulder pad 12.

In one embodiment, the distal end 31 of upper frame element 20 is fixed with respect to support structure 11. In this situation, upper frame element 20 swings but still moves substantially vertically downward. The user's head is longitudinally stationary on the head pad.

In a preferred embodiment, distal end 31 of upper frame element 20 is connected to a distal linkage element 40. The distal end 32 of distal connecting linkage 40 is fixed in one of several fixation positions identified as positions 41, 42, 43, 44 in FIG. 2. The user carefully locates distal end 32 in one of fixation positions 41-44. A lock may be provided. In operation, distal end 31 of upper frame element 20 is pivotally attached to distal frame element 40 such that the distal end of upper frame element 20 moves substantially downward y2 in a similar manner to proximal end 33 (y1) of the head pad frame 20.

FIG. 3 diagrammatically shows one embodiment of the neck traction device with a biasing element 60 spanning proximal interconnecting linkage 22 with distal linkage 40. The term "bias" refers to any mechanism which either restricts compression or restricts expansion and generates an opposing or returning force. Therefore, a spring 62 may be used as the biasing element 60 prohibiting or limiting longitudinal expansion of proximal frame element 22 with respect to distal frame element 40. Pneumatic or hydraulic spring units may be used. This limitation of longitudinal expansion has two aspects. First, it opposes the longitudinal expansion and outboard movement of shoulder pads 12, 14 operating to elongate the neck of the user. Secondly, biasing element 60 generates an opposing force to the substantially downward force of the head weight on head pad 16. A user's head normally weighs 10 pounds.

FIG. 4 diagrammatically illustrates an internal schematic of another embodiment of the present invention. In this embodiment, biasing element 64 limits the downward movement of head pad frame element 20. When the user lifts his or her head from head pad 16, biasing element 64 expands and pushes frame element 20 upward or in an opposite direction from forces y1 and y2. The upward movement retracts the shoulder frame into the support structure.

Alternatively, biasing elements 66 and 68 may be utilized. Biasing element 66 would extend from an upper portion of support structure 11 and operate on upper frame element 20. In a similar, but different manner, alternate biasing element 68 would extend from an upper point in support structure 11 and oppose the downward movement or angular of distal interlink 40.

Returning to FIG. 3, biasing element 60 may be connected to a stationary point on floor 5 of support structure 11 and operate only on shoulder frame element 24 or on the interconnecting link 22. This biasing element restricts longitudinal extension and draws back the shoulder pads upon withdrawal of the user's head weight.

In these embodiments, the head pad 16 and the head pad frame element 20 may have vertical limiters 70, 72 defining channels which establish that the head pad only moves substantially vertically such as y1, y2 with respect to stationary support structure 11. Other mechanical systems may be employed to limit the head pad to substantially vertical or near vertical movement.

In operation, the typical weight of a user's head is about 10 lbs. Traction and elongation of the user's neck occurs when the user's head is maintained in a stationary position on head pad 16 and the pads move longitudinally outboard, that is, distance x in FIG. 2, about 1 inch. By permitting the user, prior to depression of head pad 16 by the user's head, to change the position of distal end 32 of distal frame 40, the user can raise or lower the vertical height of head pad 16. Therefore, when distal end 32 is in distal fixation position 44, head pad 16 is lower in the support structure 11 than shown in FIG. 2.

It should be noted, that head pad 16 and back of neck cushion 17 may be distinct units as shown in FIG. 2 or may be one specially shaped pillow as shown in FIG. 4. Further, pillows 16, 17 may be removable for cleaning or other purposes.

The undercarriage structure (frame elements and tracks) can be various mechanical constructions. Therefore, various mechanical shapes and frames can support head pad 16. Various mechanical linkages can replace interlink connection 22. Laterally spaced support systems are not shown in the drawings. The important mechanical point is that the downward movement of head pad 16, due to the weight of the head of the user, is transformed or translated into longitudinal movement of shoulder frame element 24 and also the connected shoulder pads 12, 14.

FIG. 5 shows side pillow 90 which limits the user from removing his or her head from head pad 16 when the user is asleep. A similar side pillow is positioned on the right side of head pad 16 in FIG. 5. Further, undercarriage frame elements 92, 94 show that the frames and mechanical aspect of the undercarriage can be moved to the outer side regions of support structure 11. Therefore, the longitudinal track mounts 26, 28 in FIG. 2 can be a singular mount, can be a pair of mounts, one mount associated with each shoulder pad, or can be multiple mounts disposed on bottom floor 5 of support structure 11, proximate shoulder pads 12, 14.

FIG. 6 diagrammatically illustrates another embodiment of the present invention wherein head pads 16, 17 are supported by head support frame element 20. The support frame element 20 is connected by some mechanical support structure to a transfer or transmission module 110. The transfer or transmission 110 converts vertical movement (direction y1) into longitudinal movement x1. Drive element 112 is connected to shoulder frame element 24. To maintain the rigid longitudinal movement of shoulder pad 12, shoulder frame element 24 moves in direction x1 and then returns in direction x2 by a movement limiter which, in the illustrated embodiment, is pin 23 moving in channel 26 of track mount 28.

Associated with transfer or transmission module 110 is a bias module 120. The bias module either supplies some type of biasing force to the transmission 110 or the bias module is attached directly to the upward supports of the head pad 16 by optional mechanical linkage 122. In any event, in order to provide opposing force contrary to downward force y1, bias module 120 ultimately provides vertically upward force yr referring to the y "return" force. As discussed above, the bias module 120 may provide opposing longitudinal force in direction x2 which, via the transmission or transfer module 110, is converted into an upward bias force yr.

Transfer module 110 is also a transmission since there are several mechanical and hydraulic systems which can convert vertical downward force from head pad 16 into longitudinal force x1 directed to shoulder pad 12. For example, a set of gears converting downward force y1 into laterally extending force x1 may be employed in transfer module or transmission 110. Hydraulic systems could also be utilized although such degree of complexity is not always necessary. Chains and belts may also be employed in transfer module or transmission 110. The bias module could operate directly on drive element 112 or could operate on one or more of the chains, belts, pulleys or gears in transfer transmission module 110. Alternatively, the bias module 120 could operate on one of the vertical support elements supporting head pad 16 as shown by the dashed line 112.

The claims appended hereto are meant to cover modifications and changes within the scope and spirit of the present invention.

What is claimed is:

1. A neck traction device adapted to longitudinally elongate a user's neck with an application of force on the user's left and right shoulders while supporting the user's head in a substantially longitudinally stationary position comprising:
   a head pad for said user's head;
   a pair of shoulder pads for said user's left and right shoulders, respectively;
   said shoulder pads movably mounted on one or more longitudinal track mounts; and
   an undercarriage means for transferring a substantially downward force due to a head weight of said user's head on said head pad to a longitudinal force on said shoulder pads such that said shoulder pads, in a rest mode, are in an inboard, non-extended position in said one or more longitudinal track mounts and, in an extension mode, said are in an outboard, extended position in said one or more longitudinal track mounts;
   said undercarriage means including a head frame element, a interconnecting linkage and a shoulder pad frame element, said head pad mounted on said head frame element and said shoulder pads mounted on said shoulder pad frame element, said shoulder frame element longitudinally movably mounted in said one or more track mounts;
   said head frame element being pivotally mounted to permit substantially vertical movement due to said substantially downward force of said head weight on said head pad;
   said shoulder pad frame element pivotally mounted to said head frame element via said interconnecting linkage and said shoulder pad frame element permitted substantially longitudinal extending movement due to said substantially vertical movement of said head pad and head frame element.

2. A neck traction device as claimed in claim 1 wherein movement of said shoulder pad frame element is limited due to said one or more longitudinal track mounts.

3. A neck traction device as claimed in claim 1 including either an upward biasing element for said head frame element or a longitudinal biasing element limiting longitudinal extension of said shoulder frame element or a biasing element combining said upward bias and said limited longitudinal extension bias operatively coupled to one or both of said head frame element and said shoulder frame element or said interconnecting linkage.

4. A neck traction device as claimed in claim 3 including a support structure with one or more shoulder pad openings, said head frame element movably disposed in said support structure, a vertical limiter on said support structure within which moves said head frame element, said one or more longitudinal track mounts mounted in said support structure near said one or more shoulder pad openings.

5. A neck traction device as claimed in claim 4 wherein said head frame element includes a proximal head frame element end, connected to said interconnecting linkage, and a distal head frame element end, and wherein said interconnecting linkage is a proximal interconnecting linkage and said undercarriage means includes a distal interconnecting linkage having one end pivotally connected to said distal head frame element end, said distal head frame element end and said proximal head frame element end permitting said substantial vertical movement of said head frame element and said head pad, said distal interconnecting linkage interconnecting said distal head frame element end and said support structure.

6. A neck traction device as claimed in claim 5 wherein said distal interconnecting linkage has a first end and a second end, said first end being pivotally connected to said distal head frame element end, said second end fixed at one of several longitudinal fixation positions in said support structure.

7. A neck traction device as claimed in claim 6 wherein said distal interconnecting linkage is coupled to:
   either said upward biasing element; or said longitudinal biasing element limiting longitudinal extension; or said biasing element combining said upward bias and said limited longitudinal extension bias.

8. A neck traction device adapted to longitudinally elongate a user's neck with an application of force on the user's left and right shoulders while supporting the user's head in a substantially longitudinally stationary position comprising:
   a support structure with one or more shoulder pad openings;
   a head pad for said user's head;
   a head support frame element which supports said head pad and which is substantially vertically movably mounted in said support structure, said head support frame element having a proximal end closer to said one or more shoulder pad openings than a head support frame distal end;

a pair of shoulder pads for said user's left and right shoulders, respectively, mounted on a shoulder frame element which is longitudinally movably mounted in said support structure;

a linkage member having one linkage end pivotally connected to said head support frame proximal end and a second linkage end pivotally connected to said shoulder frame element such that a substantially downward force due to a head weight of said user's head on said head pad is transferred via said head support frame element and said shoulder frame element to a longitudinal force on said shoulder pads;

wherein shoulder frame element moves in said support structure in at least one longitudinal track converting said substantially downward force from said head weight to said longitudinal force on said shoulder pads.

9. A neck traction device as claimed in claim 8 including a longitudinal biasing element acting on said shoulder frame element opposite said longitudinal force on said shoulder pads.

10. A neck traction device as claimed in claim 8 wherein said linkage member moves in a predetermined manner due to said substantially downward force of said head weight and the device includes a biasing element countering said linkage member movement.

* * * * *